US00PP34146P2

(12) United States Plant Patent
Yencho et al.

(10) Patent No.: US PP34,146 P2
(45) Date of Patent: Apr. 19, 2022

(54) SWEETPOTATO PLANT NAMED 'NCORNSP-027SCMG'

(50) Latin Name: ***Ipomoea batatas* (L.) Lam.**
Varietal Denomination: NCORNSP-027SCMG

(71) Applicant: North Carolina State University, Raleigh, NC (US)

(72) Inventors: George Craig Yencho, Raleigh, NC (US); Kenneth Vincent Pecota, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 17/245,933

(22) Filed: Apr. 30, 2021

(51) Int. Cl.
*A01H 5/12* (2018.01)
*A01H 6/00* (2018.01)

(52) U.S. Cl.
USPC ..... Plt./258

(58) Field of Classification Search
USPC ..... Plt./258
See application file for complete search history.

*Primary Examiner* — Susan McCormick Ewoldt
(74) *Attorney, Agent, or Firm* — Myers Bigel, P.A.

(57) ABSTRACT

'NCORNSP-027SCMG' is a compact, non-twining, semi-upright variety producing many short shoots. It is distinguishable from other cultivars by its palmate, deeply lobed leaves with 5-9 lobes, a compact habit, and semi-erect mounding plant architecture. The yellow-green (RHS 144B) leaves, deep-lobing, quantity of lobes, short internodes, and the plant architecture are what make 'NCORNSP-027SCMG' unique amongst the current ornamental sweetpotatoes in the marketplace. 'NCORNSP-027SCMG' also exhibits good vigor, is very well branched, and exhibits a growth habit that promotes good plant production in the greenhouse for wholesale distributors.

8 Drawing Sheets

Latin name of the genus and species: The Latin name of the novel, ornamental plant variety disclosed herein is *Ipomoea batatas* (L.) Lam.

Variety denomination: The inventive cultivar of *Ipomoea batatas* disclosed herein has been given the varietal denomination 'NCORNSP-027SCMG'.

BACKGROUND OF THE INVENTION

*Ipomoea batatas* is a member of the morning glory family Convolvulaceae. This species is grown worldwide and it exhibits a wide range of plant forms and colors. The cultivated members of *Ipomoea batatas* grown by farmers worldwide are commonly produced for consumption of their nutritious, enlarged storage roots. These types typically produce a fast growing green vine that has a wide variety of leaf shapes ranging from palmate and deeply lobed, to cordate or triangular shaped leaves with no lobes.

Like their edible forms, *Ipomoea batatas* ornamental sweetpotato plants are a heat-loving, drought-tolerant, perennial vine typically grown as an annual. However, ornamental sweetpotato plants are distinguished from the edible cultivated forms in that they often do not produce attractive, enlarged storage roots suitable for human consumption. Instead, they possess unique foliage colors, leaf shapes, and growth habits, which have significant value in the ornamental marketplace.

Ornamental sweetpotatoes are desirable in the landscape and ornamental industries because their foliage comes in a wide variety of colors (e.g., pale yellow to dark purple with some exhibiting temporal and individual leaf color variegation patterns) and plant shapes (e.g., mounded and very compact to prostrate and highly spreading). They can be grown in a potted plant and/or mixed planting format, and they have the ability to cover a large space or hang over walls and decorative pots creating brightly colored and textured backdrops in gardens and patios. Most ornamental sweetpotatoes grow and last the entire growing season and they require little maintenance. Moreover, these plants have few insect or disease problems.

To meet the growing horticultural demand for ornamental sweetpotatoes, it is desirable to produce new cultivars of ornamental sweetpotato with new or improved foliage colors, variegation patterns, leaf shapes, and plant architectures. In addition, it would be advantageous to develop cultivars of ornamental sweetpotato exhibiting a more compact growth that do not out-compete other species in mixed containers.

'NCORNSP-027SCMG' was bred to meet the increasing demand for new ornamental sweetpotatoes. 'NCORNSP-027SCMG' is a compact, non-twining, upright variety producing many short shoots. It is distinguishable from other ornamental sweetpotato cultivars by its palmate, deeply lobed leaves with 5-9 lobes, a compact habit and semi-erect mounding plant architecture. The yellow-green (RHS 144B) leaves, short internodes, and the plant architecture, which promotes good plant production in the greenhouse for wholesale distributors, distinguishes 'NCORNSP-027SCMG' amongst the current ornamental sweetpotatoes in the marketplace. 'NCORNSP-027SCMG' exhibits very good vigor and is very well branched. In greenhouse and field trials conducted since 2016 by the breeding program and industry collaborators 'NCORNSP-027SCMG' has been shown to be much less vigorous than *Ipomoea batatas* 'Margarita' and 'Blackie' and is suitable for use as a landscape or containerized plant. 'NCORNSP-027SCMG' has not been observed to produce flowers under short- or long-day conditions.

Lineage. 'NCORNSP-027SCMG' (breeding designation NC9174-005ORN) originated from hand-pollinated seed from the proprietary *Ipomoea batatas* breeding lines NC8720-027ORN (the female parent; not patented) and NC8568-001ORN (the male parent; not patented). Botanical seed was harvested from ornamental lines grafted onto a flower-inducing *I. setosa* sweetpotato line in greenhouses between October 2014 and April 2015 in Raleigh, N.C. NC8720-027ORN resulted from hand-pollinated seed harvested from the proprietary *Ipomoea batatas* breeding lines NC8148-006ORN (the female parent; not patented) and NC8124-001ORN (the male parent; not patented). NC8568-001ORN resulted from open pollinated seed collected from NC8249-010ORN (the female parent; not patented). Botanical seed from this family were planted in the greenhouse in December 2015. The first cycle of selection on the population was exercised at the seedling tray stage and each survivor was transferred to a single 6-inch pot, which was then maintained in the greenhouse. Cuttings (2 each) were taken from the plants in April and planted in the field as unreplicated 2-plant plots, during mid-June 2016. The single, individual plant now known as 'NCORNSP-027SCMG' was selected Sep. 25, 2016 because of its combination of exceptional features, and it has been propagated asexually since that time.

Asexual Reproduction. Since its selection, *Ipomoea batatas* 'NCORNSP-027SCMG' has been asexually reproduced in Raleigh, N.C. predominantly by vegetative propagation of vine cuttings. Successively, there have been seven cycles of vegetative propagation, one cycle of tissue culture micropropagation, and multiple vegetative propagation cycles to increase plant numbers. Asexual reproduction of 'NCORNSP-027SCMG' by cuttings has shown that the unique features of the new cultivar are stable and the plant reproduces true to type in successive generations.

SUMMARY OF THE INVENTION

'NCORNSP-027SCMG' is a compact, non-twining, semi-upright variety producing many short shoots. It is distinguishable from other cultivars by its palmate, deeply lobed leaves with 5-9 lobes, a compact habit and semi-erect mounding plant architecture. The yellow-green (RHS 144B) leaves, deep lobing, quantity of lobes, short internodes, and the plant architecture distinguishes 'NCORNSP-027SCMG' amongst the current ornamental sweetpotatoes in the marketplace. 'NCORNSP-027SCMG' also exhibits good vigor and is very well branched, a growth habit that promotes good plant production in the greenhouse for wholesale distributors. In greenhouse and field trials conducted since 2016, 'NCORNSP-027SCMG' has been shown to be a much less vigorous vine producer than *Ipomoea batatas* 'Margarita' and 'Blackie' and is suitable for use as a landscape or containerized plant. 'NCORNSP-027SCMG' has not been observed to produce flowers under short- or long-day conditions.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which more accurately describe the colors of the new *Ipomoea batatas*.

DETAILED BOTANICAL DESCRIPTION OF THE NEW VARIETY

Figure 1:
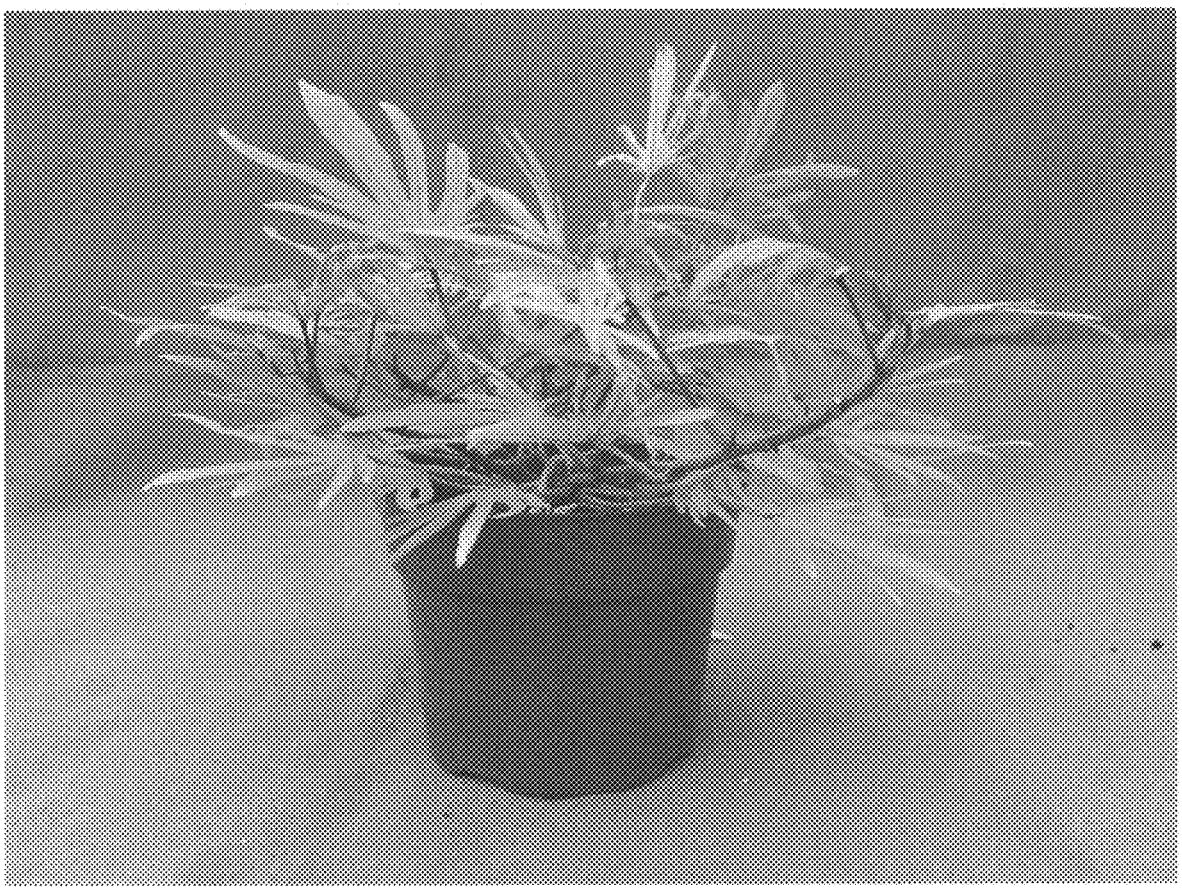
FIG. 1 is a color photograph of a typical specimen of greenhouse grown *Ipomoea batatas* 'NCORNSP-027SCMG' in a 6-inch pot from the side, 55 days after planting.
Figure 2:
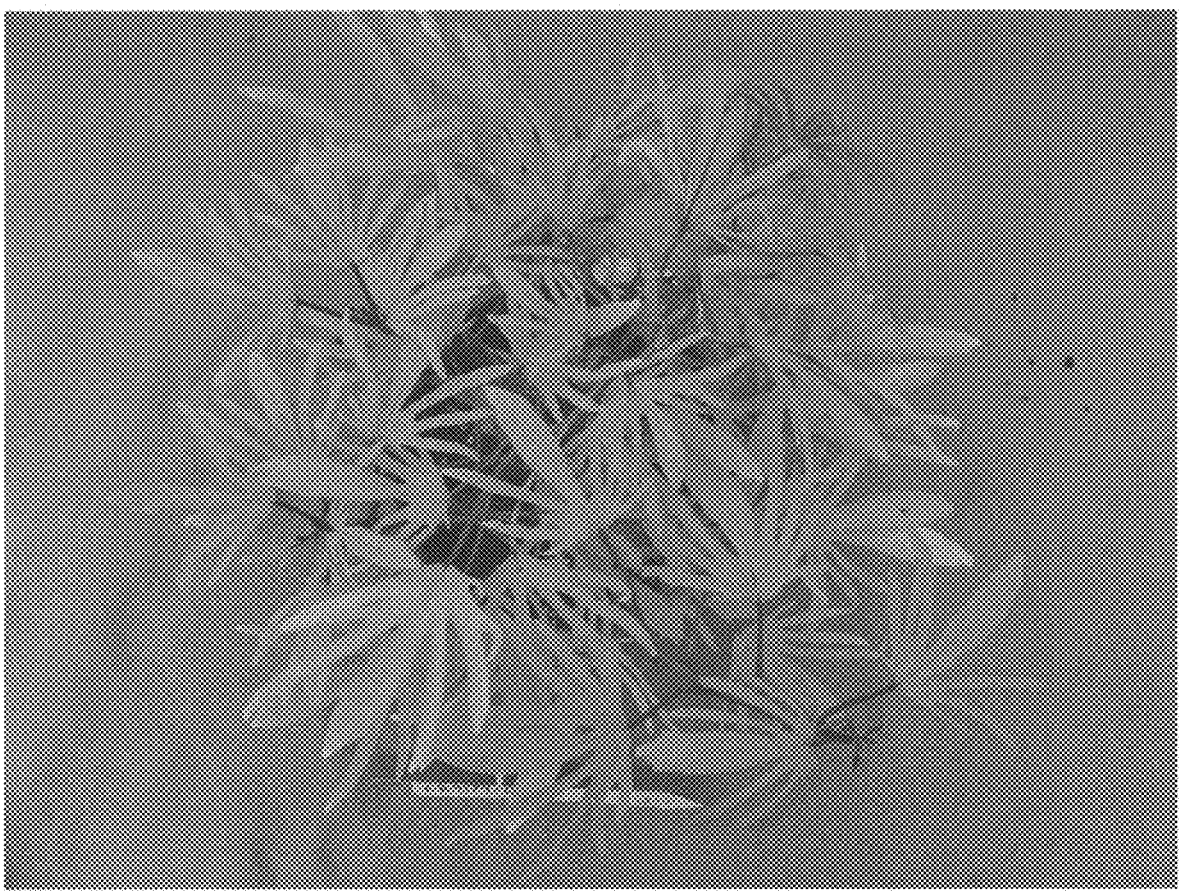
FIG. 2 is a color photograph of a typical specimen of greenhouse grown *Ipomoea batatas* 'NCORNSP-027SCMG' in a 6-inch pot from the top, 55 days after planting.
Figure 3:
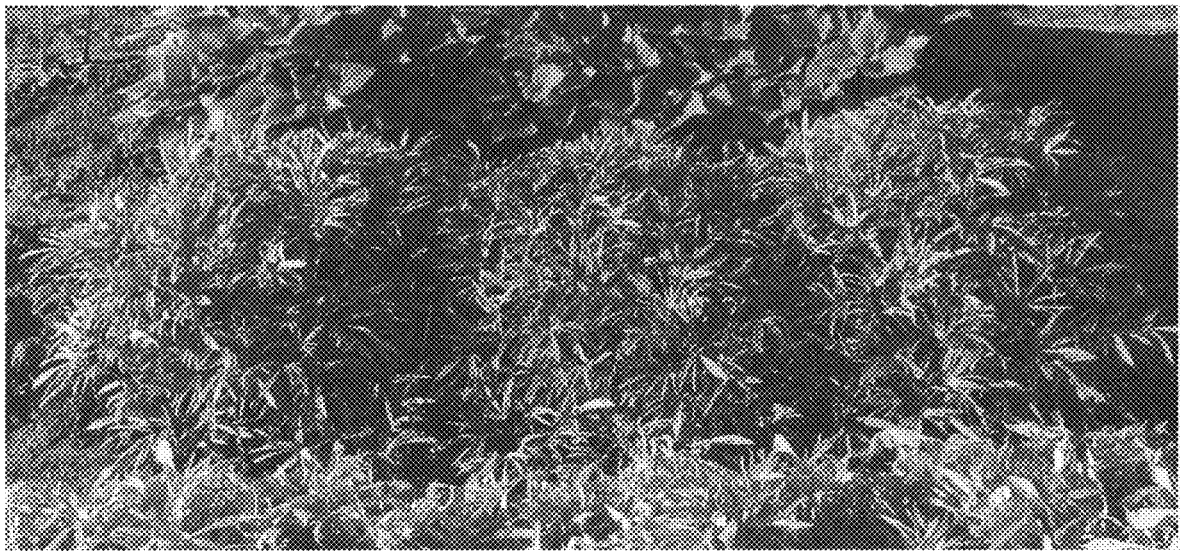
FIG. 3 is a color photograph of a typical specimen of *Ipomoea batatas* 'NCORNSP-027SCMG' from the side in the field, 68 days after planting.
Figure 4:
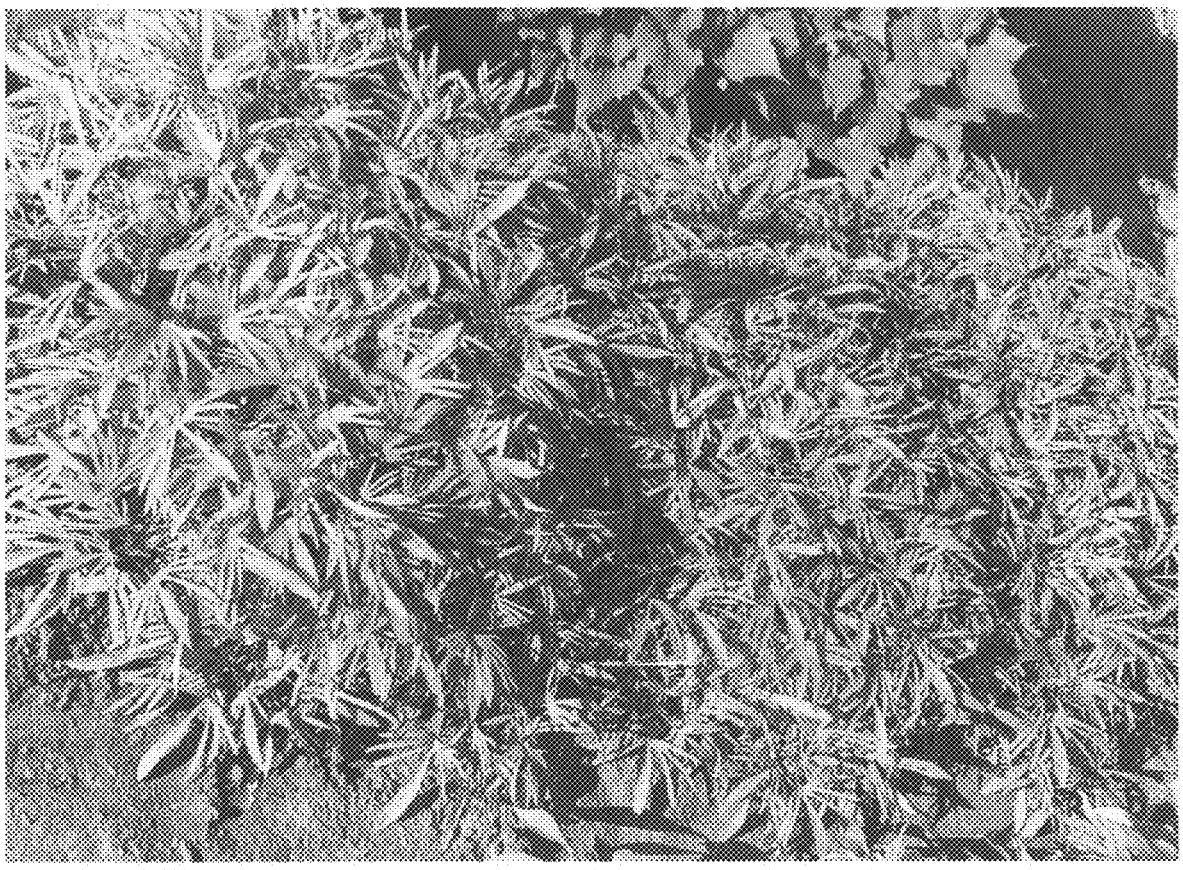
FIG. 4 is a color photograph of a typical specimen of *Ipomoea batatas* 'NCORNSP-027SCMG' from the top in the field, 68 days after planting.
Figure 5:
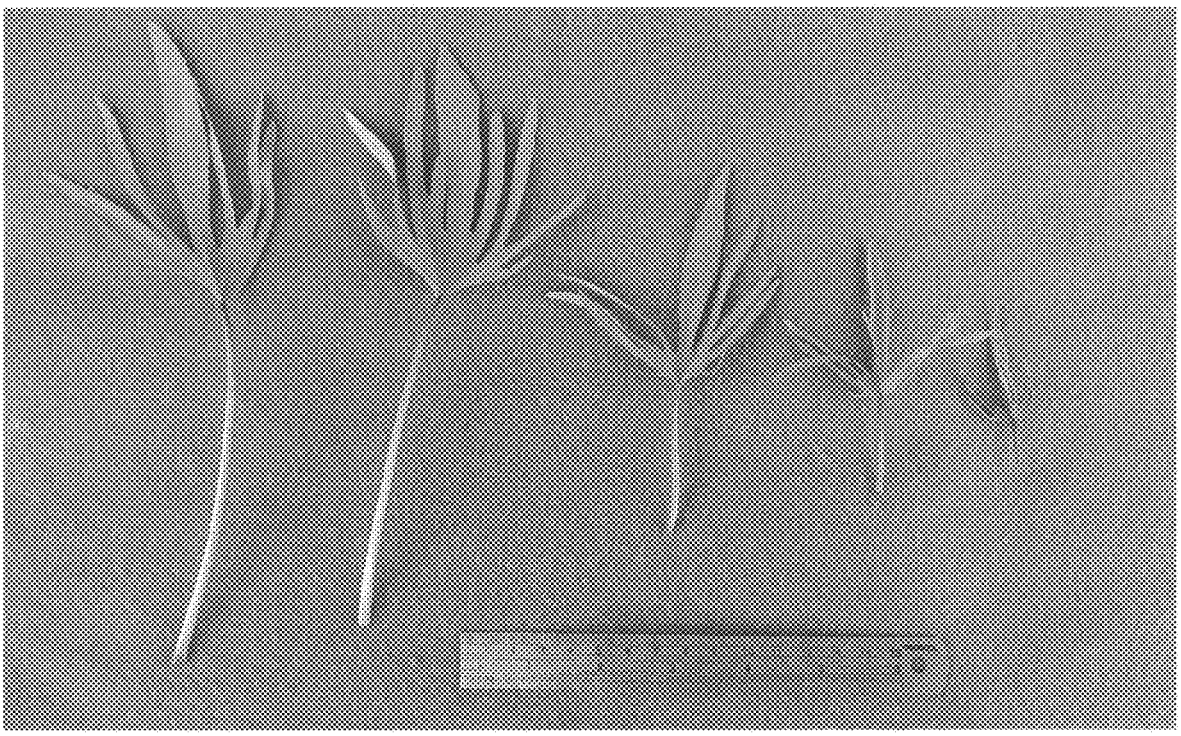
FIG. 5 is a color photograph showing the upper (top) surfaces of leaves of varying degrees of maturity that are produced by *Ipomoea batatas* 'NCORNSP-027SCMG', with the far-left leaf being a mature leaf at 65 days after planting.
Figure 6:
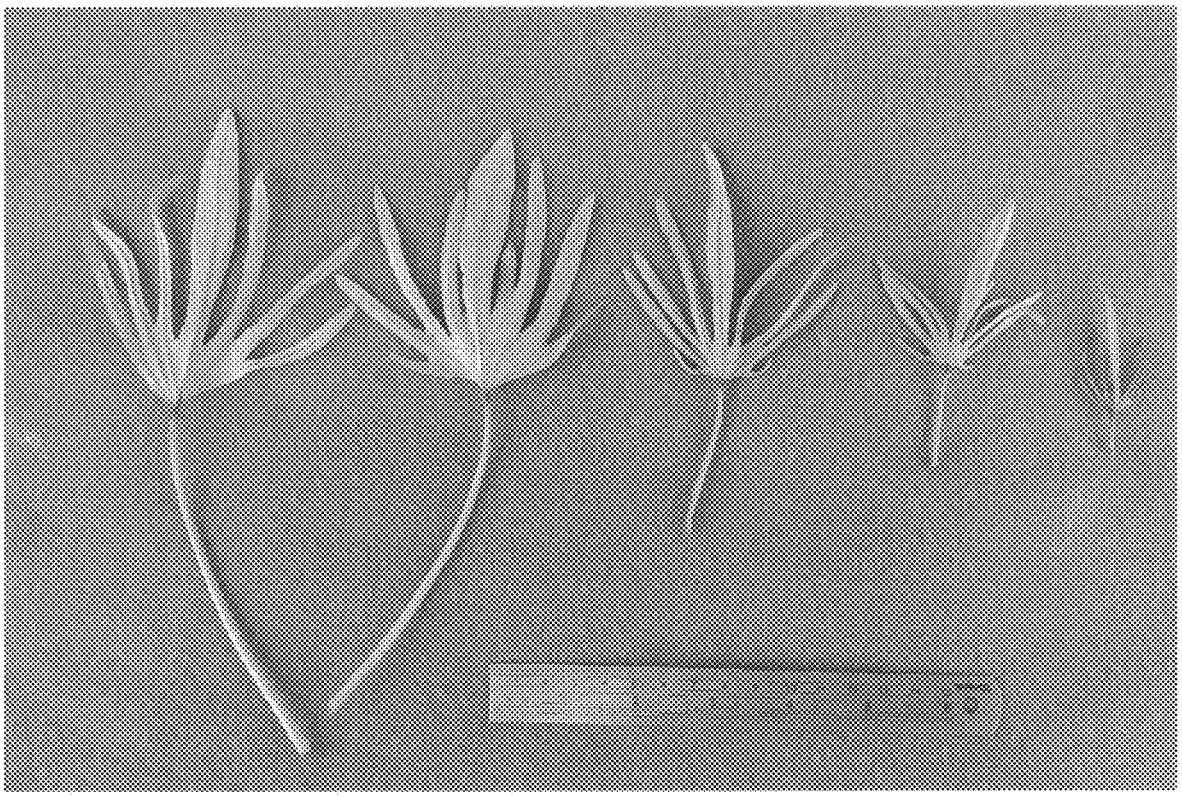
FIG. 6 is a color photograph showing the lower (bottom) surfaces of leaves of varying degrees of maturity that are produced by *Ipomoea batatas* 'NCORNSP-027SCMG', with the far-left leaf being a mature leaf at 65 days after planting.

The following is a detailed description of the botanical characteristics of a new and distinct cultivar of *Ipomoea batatas* plant known by the cultivar name 'NCORNSP-027SCMG'. All colors cited herein refer to The Royal Horticulture Society Colour Chart designations (The Royal Horticultural Society, London, 1995, $4^{th}$ ed.) except where general terms of ordinary dictionary significance are used. Plant descriptions are based on the standardized international sweetpotato descriptors established jointly by the International Potato Center (CIP), Lima, Peru; The Asian Vegetable Research and Development Center (AVRDC), Taipei, Taiwan; and the International Board for Plant Genetics Resources (IBPGR), Rome, Italy (CIP, AVRDC, IBPGR. 1991. Descriptors for Sweet Potato. Huaman, Z., editor. International Board for Plant Genetic Resources, Rome, Italy, 134pp.). Where dimensions, sizes, colors, and other characteristics are given, it is to be understood that such characteristics are approximations or averages set forth as accurately as practicable.

The descriptions reported herein are from a group of 55-day-old specimens grown individually in six-inch azalea pots. The plants were grown in Raleigh, N.C., under commercial practice in a glass-covered greenhouse, where, during the fall, day and night temperatures range between 30-40° C. and 22-26° C., respectively. After rooting, plants were treated with 200 ppm 20-10-20 fertilizer weekly. Plant histories were taken in April 2020 in Raleigh, N.C. *Ipomoea batatas* 'NCORNSP-027SCMG' has not been observed under all possible environmental conditions; therefore, the phenotype may vary under different environmental conditions such as season, temperature, light intensity, day length, cultural conditions, and the like, without however, any variance in the genotype.

Classification:

*Botanical name.*—*Ipomoea batatas* (L.) Lam.

*Common name.*—Ornamental Sweetpotato.

*Variety name.*—'NCORNSP-027SCMG'.

Growth conditions: *Ipomoea batatas* 'NCORNSP-027SCMG' has very good vigor and a moderate growth rate. In locations with mild winter conditions, *Ipomoea batatas* 'NCORNSP-027SCMG' will grow perennially; otherwise, it is an annual plant. Similar to other cultivated sweetpotatoes, wind or rain rarely cause much damage to 'NCORNSP-027SCMG', but if damage does occur, the plant drops the damaged leaves and grows new shoots at nodes where the leaves were lost. Under low light levels in a greenhouse, 'NCORNSP-027SCMG' can develop intumescence, which will remain on the affected foliage, but will be outgrown with new foliage.

Aboveground structure and coloration: FIGS. 1, 2, 3, 4, 5, and 6 show the shape and coloration of a typical specimen of *Ipomoea batatas* 'NCORNSP-027SCMG'. Color may vary somewhat due to temperature and nutrient stress. Overall, this cultivar is a compact, non-twining, semi-upright herbaceous plant that has an average height of ~13.8 cm and an average area spread of ~35.6 cm. The growth habit of this plant is to grow upright with shoots growing upward and outward.

Branches:

*Branching habit.*—Freely-branching with ~5-6 primary lateral branches coming off the stem. Very dense foliage and no pinching is required to stimulate branching. Branch texture is smooth and glabrous with slight pubescence.

*Vegetative lateral branching.*—Length: ~12.3 cm. Diameter: ~0.4 cm. Internodes are short with an average length of ~0.9 cm.

*Secondary lateral shoots.*—No measurable secondary lateral shoots formed on the rated plants.

*Stem.*—Round and smooth with an upward, very strong, slightly flexible, non-brittle strength. Color: Greyed-Purple (RHS N186B).

*Adventitious roots.*—Absent at nodes.

*Petiole.*—Petioles are held slightly upward and curve outward. Leaf petiole has a smooth glabrous texture. Length: ~7.1 cm. Diameter: ~0.2 cm. Color: Yellow-Green (RHS 144B) and Purple (RHS N77C) near lamina base.

Foliage: Leaves are alternate and tend to slightly spiral around the stem. They are simple and heavily divided into 5-9 lobes. Leaf shape is somewhat variable as is size. (see FIGS. 5 and 6).

*Quantity.*—Heavily foliated, with ~22.5 leaves per lateral branch.

*Mature leaf length.*—~7.7 cm.

*Mature leaf width.*—~9.5 cm.

*Leaf margin.*—Entire.

*Leaf apex.*—Acuminate.

*Leaf shape.*—Very deeply lobed, with linear leaf lobing.

*Leaf texture.*—Glabrous texture and matte finish.

*Venation.*—Arcuate to cross-venulate. Texture: Glabrous.

*Color.*—Leaves are yellow-green (RHS144B) and range within that palate as they mature. See also Table 1.

TABLE 1

Leaf color of *Ipomoea batatas* 'NCORNSP-027SCMG'.

| Leaf Structure | Upper Surface | Lower Surface |
|---|---|---|
| Mature Leaf | Yellow-Green (RHS 144B) | Yellow-Green (RHS 144D) |
| Young Leaf | Yellow-Green (RHS 144B) | Yellow-Green (RHS 144B) |
| Vein - mature leaf | Yellow-Green (RHS 145B) | Yellow-Green (RHS 145D) |
| Vein - young leaf | Purple (RHS N79C) | Purple (RHS 79A) |

Inflorescence: The production of flowers by 'NCORNSP-027SCMG' is rare and flowers have not been obtained for the measurement of flower traits.

Figure 7:
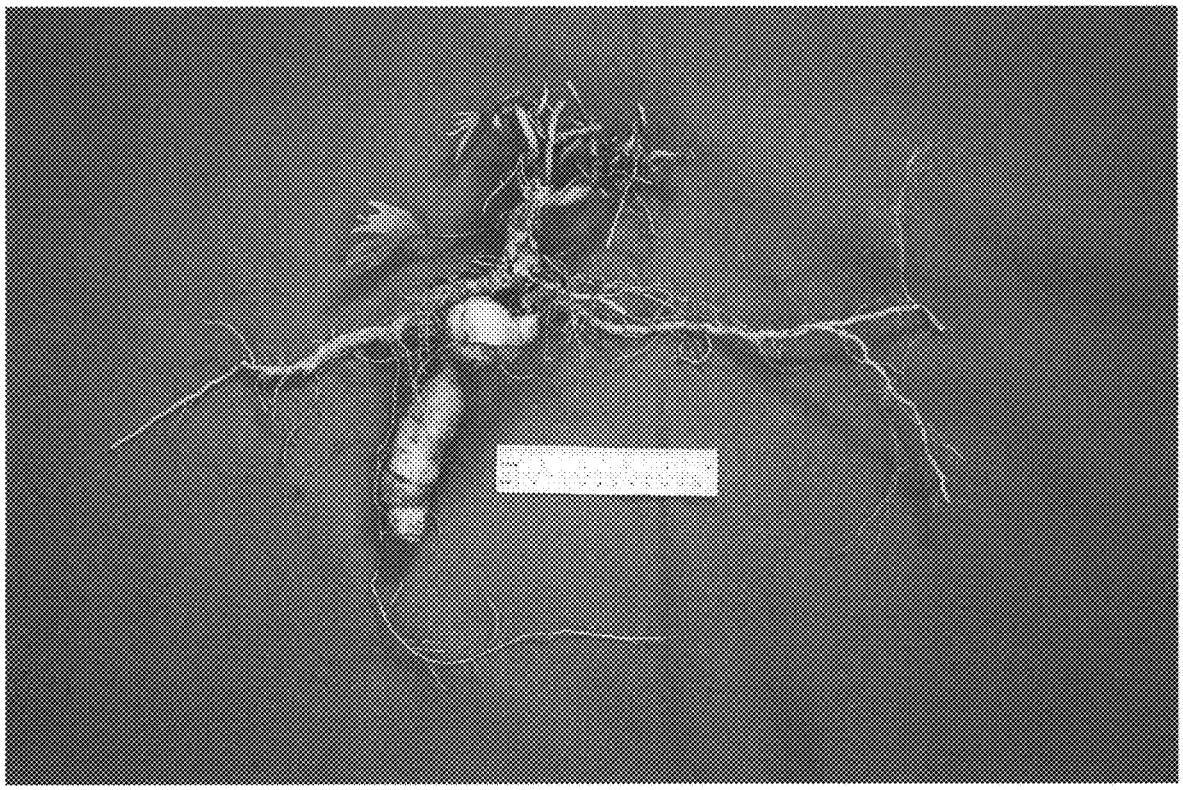
FIG. 7 is a color photograph showing the storage roots produced by *Ipomoea batatas* 'NCORNSP-027SCMG' in the field, 130 days after planting.
Figure 8:
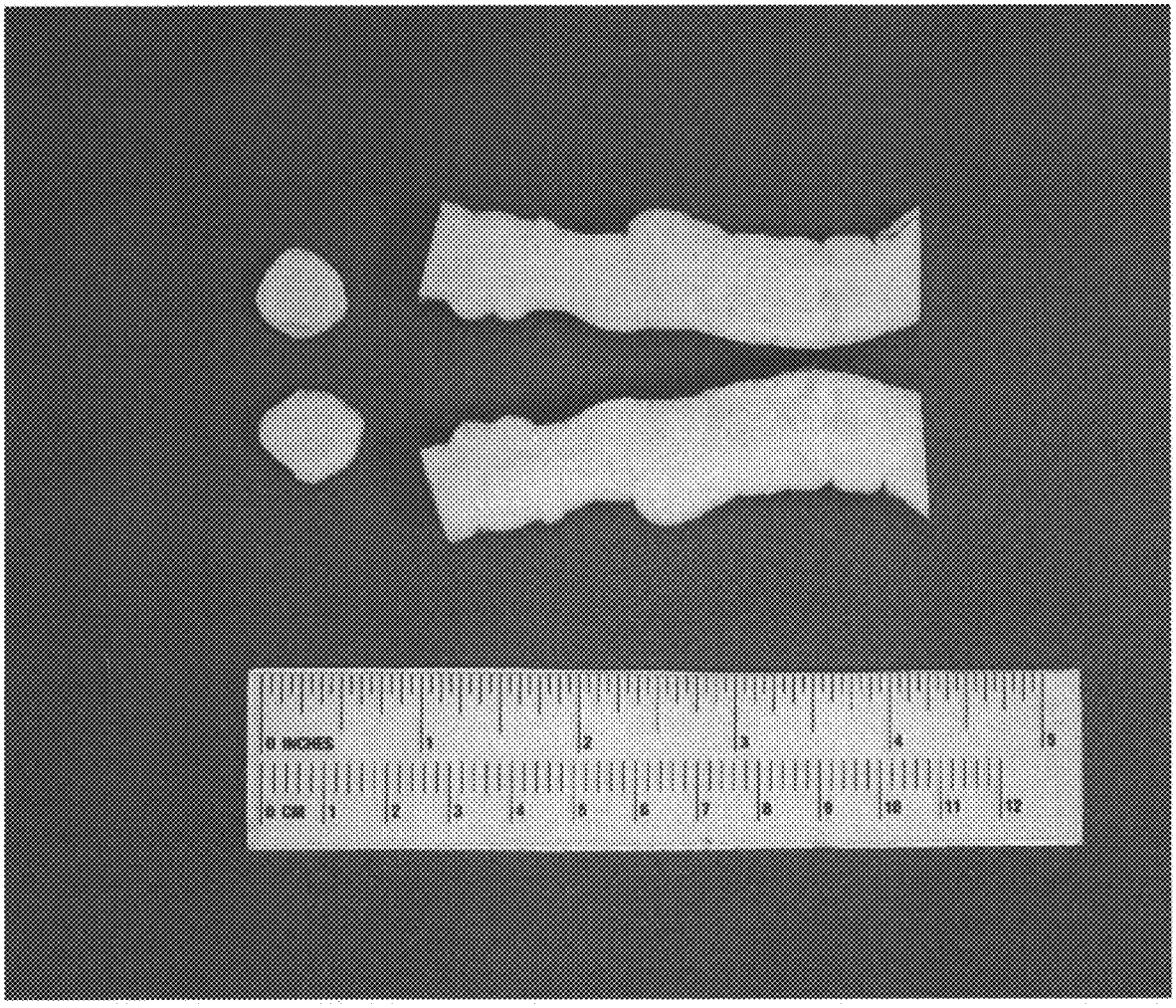
FIG. 8 is a color photograph showing cross sections in the length and width directions of storage roots produced by *Ipomoea batatas* 'NCORNSP-027SCMG' in the field, 130 days after planting.

Storage root coloration: *Ipomoea batatas* 'NCORNSP-027SCMG' generally does not produce underground storage roots, but if they are formed, the storage roots are typically small and malformed and do not meet USDA Sweetpotato Storage Root Grade Standards (see FIGS. 7 and 8). Fibrous roots are typically cream (RHS 155B). Storage roots that are formed generally possess cream skin and a white flesh, but these colors are subject to soil characteristics and are not considered diagnostic features of the plant.

Disease or pest resistance: 'NCORNSP-027SCMG' is susceptible to whiteflies and thrips in a greenhouse environment. 'NCORNSP-027SCMG' is susceptible to damage by Japanese beetles (*Popillia japonica*) under outdoor conditions. The susceptibility of 'NCORNSP-027SCMG' to other known insects and pathogens of sweetpotato is unknown. Under low light conditions, slight edema may occur.

COMPARISON WITH OTHER *IPOMOEA BATATAS* CULTIVARS

'NCORNSP-027SCMG' is distinct based on leaf shape and plant architecture. Of the common cultivars of ornamental sweetpotato, 'NCORNSP-027SCMG' is best compared with the 'NCORNSP-012EMLC' (U.S. Plant Pat. No. 21,744) and 'NCORNSP-025SCK' (U.S. Plant Pat. No. 31,855) cultivars (Table 2). Like both 'NCORNSP-012EMLC' and 'NCORNSP-025SCK', 'NCORNSP-027SCMG' has yellow-green leaves. However, the leaf lobes of 'NCORNSP-027SCMG' are significantly deeper than NCORNSP-025SCK. 'NCORNSP-027SCMG' has more lobes per leaf than either 'NCORNSP-012EMLC' or 'NCORNSP-025SCK'. The lobes of 'NCORSP-027SCMG' are largely linear in shape, whereas the lobes of NCORNSP-012EMLC are narrowly oblanceolate. The habit of 'NCORNSP-027SCMG' is more compact than either 'NCORNSP-012EMLC' or 'NCORNSP-025SCK'. In contrast to 'NCORNSP-012EMLC' and 'NCORNSP-025SCK', which occasionally produce flowers under short-day lengths, 'NCORNSP-027SCMG' rarely produces flowers under any day length.

'NCORNSP-027SCMG' is distinct from its parents, 'NC8720-027ORN' and 'NC8568-001ORN', by its leaf lobing and structure. 'NCORNSP-027SCMG' has more lobes per leaf than either 'NC8720-027ORN' (which has 5-7 lobes) or 'NC8568-001ORN' (which has 3-5 lobes). 'NCORNSP-027SCMG' is more deeply lobed than either 'NC8720-027ORN' or 'NC8568-001ORN'. 'NCORNSP-027SCMG' is also more compact than 'NC8568-001ORN', which has a slight trailing habit.

TABLE 2

Comparison of 'NORNSP-027SCMG' with other *Ipomoea batatas* cultivars.

| Characteristic | 'NORNSP-027SCMG' | 'NORNSP-012EMLC' | 'NORNSP-025SCK' |
|---|---|---|---|
| Plant Habit | Compact, semi-upright and mounding habit | Compact, semi-upright and mounding habit | Moderately compact to compact, slightly upright and mounding habit |
| Average Leaf Length and Width | Length: 7.7 cm Width: 9.5 cm | Length: 14.0 cm Width: 15.5 cm | Length: 10.3 cm Width: 9.9 cm |

TABLE 2-continued

Comparison of 'NORNSP-027SCMG' with other *Ipomoea batatas* cultivars.

| Characteristic | 'NORNSP-027SCMG' | 'NORNSP-012EMLC' | 'NORNSP-025SCK' |
|---|---|---|---|
| Foliage Color | Yellow-Green (RHS 144B) | Yellow-green (RHS N144C) | Yellow-green (RHS 144B-C) |
| Leaf Shape | Deeply lobed, 5-9 lobes. Entire with an acuminate apex and a lobed base. | Deeply lobed, 5-7 lobes. Entire with an acuminate apex and a cordate base. | Moderately lobed, 3-5 lobes. Entire with an acuminate apex and a lobed base. |

We claim:

1. A new and distinct cultivar of *Ipomoea batatas* plant named 'NCORNSP-027SCMG', substantially as illustrated and described herein.

* * * * *